United States Patent [19]
Hüper et al.

[11] 3,941,756
[45] Mar. 2, 1976

[54] WATER-INSOLUBLE PREPARATIONS OF PEPTIDE MATERIALS, THEIR PRODUCTION AND THEIR USE

[75] Inventors: Fritz Hüper; Erich Rauenbusch; Günter Schmidt-Kastner, all of Wuppertal; Bruno Bömer, Leverkusen; Herbert Bartl, Odenthal-Hahnenberg, all of Germany

[73] Assignee: Bayer Aktiengesellschaft, Leverkusen, Germany

[22] Filed: June 20, 1974

[21] Appl. No.: 481,225

Related U.S. Application Data

[62] Division of Ser. No. 345,452, March 27, 1973, Pat. No. 3,871,964.

[30] Foreign Application Priority Data
Mar. 20, 1972  Germany............................ 2215687

[52] U.S. Cl..... 260/78.5 R; 260/78.5 BB; 260/80.8; 260/80.81
[51] Int. Cl.$^2$................ C08F 220/20; C08F 222/04
[58] Field of Search... 260/78.5 R, 78.5 BB, 89.5 A, 260/80.8, 80.81

[56]     References Cited
         UNITED STATES PATENTS

| | | | |
|---|---|---|---|
| 2,894,921 | 7/1959 | Jones................................ | 260/17.4 |
| 2,923,692 | 2/1960 | Ackerman et al................. | 260/17.4 |
| 3,218,305 | 11/1965 | Krieble............................. | 260/89.5 |
| 3,297,664 | 1/1967 | Miskel et al...................... | 260/80.3 |
| 3,586,646 | 6/1971 | Corte et al....................... | 260/2.2 R |
| 3,711,574 | 1/1973 | Jaworek et al.................. | 260/878 R |

*Primary Examiner*—John Kight, III
*Attorney, Agent, or Firm*—Depaoli & O'Brien

[57]     ABSTRACT

There are disclosed water-insoluble proteinic preparations in which a protein or polypeptide is bound to a copolymer, which preparations are useful for binding enzymes in order to carry out enzyme-catalyzable reactions. These preparations comprise a peptide material bound to a crosslinked copolymer comprising the following copolymerized units:
 A. about 0.1 to 30 wt. % of at least one α,β-monoolefinically unsaturated dicarboxylic acid anhydride having about 4 to 9 carbon atoms;
 B. about 35 to 90 wt. % of at least one di- and/or poly(meth)acrylate of a diol and/or polyol as hereinafter defined; and
 C. about 5 to 60 wt. % of at least one hydrophilic monomer, the copolymer having a bulk volume of 1.4 to 30 ml/g and a specific surface area of about 1 to 500 m$^2$/g, and containing, after saponification of the anhydride groups, about 0.01 to 14 milliequivalents of acid per gram.

2 Claims, No Drawings

WATER-INSOLUBLE PREPARATIONS OF PEPTIDE MATERIALS, THEIR PRODUCTION AND THEIR USE

This is a division of application Ser. No. 345,452, filed Mar. 27, 1973, now U.S. Pat. No. 3,871,964.

BACKGROUND OF THE INVENTION

1. Field of the Invention

The invention relates to new water-insoluble proteinic preparations in which a protein or polypeptide is bound to a copolymer, to a process for the production of these new preparations, and to their use for carrying out enzyme-catalyzable reactions.

2. Description of the Prior Art

The covalent bonding of substances to insoluble polymeric carriers has gained increasingly in importance in recent years. The binding of catalytically active compounds, for example enzymes, offers particular advantages since they can, in this form, be easily separated off after completion of the reaction and repeatedly reused.

Copolymers of maleic anhydride and vinyl compounds have already been proposed repeatedly as carriers with suitable binding groups. However, copolymers of maleic anhydride with ethylene and monovinyl compounds become more or less water-soluble on reaction with aqueous enzyme solutions so that before or during the reaction, an additional crosslinking agent, for example a diamine, is desirably added. Enzyme preparations obtained in this way are relatively difficult to filter and possess soluble constituents, and losses of bound enzyme results (compare E. Katchalski, Biochemistry 3, (1964), pages 1905-1919).

Further, copolymers of acrylamide and maleic acid have been described which are converted into the anhydride form by subsequent heating. These products are relatively slightly crosslinked, swell very markedly in water and only possess moderate mechanical stability which leads to abrasion losses when using these resins (compare German Offenlegungsschrift 1 908 290).

Furthermore, strongly crosslinked carrier polymers have been produced by copolymerization of maleic anhydride with divinyl ethers. Because of the alternating type of copolymerization of the monomers, these polymers contain a very high proportion of anhydride groups - in each case above 50 % by weight of maleic anhydride, in the examples disclosed - which is determined by the molecular weight of the vinyl ether monomer and is therefore only adaptable to the particular end use within relatively narrow limits (compare German Offenlegungsschrift 2 008 996).

We have therefore attempted to find new reaction products of proteins and peptides with new, strongly crosslinked, water-swellable copolymers possessing a content of cyclic dicarboxylic acid anhydride groups capable of great variation, and a convenient process for their production. The new reaction products of proteins and peptides with the new copolymers do not have the disadvantages of the previously known protein preparations or at least, have them to a slighter extent.

SUMMARY OF THE INVENTION

There is provided according to this invention, a water-insoluble preparation comprising a peptide material bound to a crosslinked copolymer comprising the following copolymerized units:

A. about 0.1 to 30 wt. %, preferably 2 to 20 wt. % of at least one $\alpha$, $\beta$-monoolefinically unsaturated dicarboxylic acid anhydride having about 4 to 9 carbon atoms, preferably 4 to 5 carbon atoms;

B. about 35 to 90 wt. %, preferably 50 to 85 wt. %, of at least one di- and/or poly(meth)acrylate of a diol and/or a polyol as hereinafter defined; and C. about 5 to 60 wt. %, preferably 10 to 50 wt. %, of at least one hydrophilic monomer not the same as defined under B; the copolymer having a bulk volume of about 1.4 to 30, preferably 2 to 20 ml/g, and a specific surface area of 1 to 500 m$^2$/g, preferably 1 to 400 m$^2$/g and containing, after saponification of the anhydride groups, 0.01 to 14, preferably 0.02 to 11, milliequivalents of acid per gram.

We also provide according to the invention a process for the production of a preparation as defined above in which, relative to the total weight of copolymerizable monomers present:

A. about 0.1 to 30 wt. %, preferably 2 to 20 wt. %, of the said at least one anhydride;

B. about 35 to 90 wt. %, preferably 50 to 85 wt. %, of the said at least one acrylate; and C. about 5 to 60 wt. %, preferably 10 to 50 wt. %, of the said at least one hydrophilic monomer;

are copolymerized by precipitation or bead polymerization in a diluent inert to anhydride groups at a temperature of 20° to 200°C. in the presence of a free-radical initiator and the copolymer thus produced is reacted, in aqueous suspension, with a solution of the peptide material to give the desired preparation.

Finally, we also provide according to this invention a process for carrying out an enzyme-catalyzed conversion of a substrate comprising contacting a preparation as defined above in which the peptide material is an enzyme with a substrate for the enzyme under conditions where the said conversion occurs.

DESCRIPTION OF PREFERRED EMBODIMENTS

In this specification the term "peptide material" includes proteins, polypeptides, oligopeptides, and aminoacids as understood in the art to which this invention pertains.

The starting materials required for the production of the preparations of the invention will first be described.

Important examples of $\alpha,\beta$-monoolefinically unsaturated dicarboxylic acid anhydrides with 4-9 carbon atoms, preferably with 4-5 carbon atoms, which are required to provide units A are maleic, itaconic and citraconic anhydrides, especially maleic anhydride. Mixtures of these anhydrides can also be used for the copolymerization.

The diols and polyols from which the dimethacrylates, polymethacrylates, diacrylates and polyacrylates used to provide units B in this invention are derived comprise the following categories of compounds:

i. at least dihydroxy compounds with at least two alcoholic or phenolic, preferably alcoholic, hydroxyl groups;

ii. the reaction products of the said at least dihydroxy compounds (i) with alkylene oxides having 2 to 8, preferably 2 to 4 carbon atoms, or mixtures of such alkylene oxides, 1 to 10$^4$, preferably 1 to 10, alkylene oxide units being added to one mol of the at least dihydroxy compound (i). Examples of suitable alkylene oxides are ethylene oxide, propylene oxide, butylene oxide, trimethylene oxide, tetramethylene oxide, bischloromethyl-oxacyclobutane and styrene oxide, ethylene and propylene oxides being preferred;

iii. the reaction products of at least one of the alkylene oxides defined in (ii) with a compound having at least two Zerewitinoff-active hydrogen atoms which is not an alcohol or a phenol.

The di- and poly(meth)acrylates of diols and polyols, to be employed according to the invention, can be obtained in accordance with known methods, for example by reaction of the diols and/or polyols with (meth)acrylic acid chloride in the presence of about equimolar amounts, relative to acid chloride, of tertiary amines such as triethylamine, at temperatures below 20°c. in the presence of benzene (compare German Offenlegungsschrift 1 907 666). Possible diols or polyols with at least 2 carbon atoms, preferably 2-12 carbon atoms, are, for example: ethylene glycol, 1,2-propanediol, 1,3-propanediol, butanediols, especially 1,4-butanediol, hexanediols, decanediols, glycerine, trimethylolpropane, pantaerythritol, sorbitol, sucrose and their reaction products with alkylene oxides, as indicated above. Poly-bis-chloromethyl-oxacyclobutane or polystyrene oxide are also suitable. Mixtures of diols and polyols can also be employed to produce the acrylates.

Preferably, diacrylates or dimethacrylates of diols with 2-4 carbon atoms and/or reaction products of one mol of these diols with 1-10 mols of alkylene oxide with 2-4 carbon atoms or trimethylolpropane trimethacrylate are used.

The dimethacrylates of ethylene glycol, diethylene glycol, triethylene glycol, tetraethylene glycol or higher polyalkylene glycols with molecular weights of up to 500, or their mixtures, are particularly advantageous.

The third group of the copolymerization components, giving residues C, consists of singly unsaturated, hydrophilic monomers. As such, it is possible to use any polymerizable singly unsaturated compound which does not possess any functional groups which are reactive towards anhydride groups, and which forms hydrophilic polymers.

The hydrophilic monomers C preferably possess at least one carboxyl, aminocarbonyl, sulpho or sulphamoyl group, and the amino groups of the aminocarbonyl or sulphamoyl radical can optionally carry as substituents alkyl groups with 1-4 carbon atoms or alkoxymethyl groups with 1-4 carbon atoms in the alkoxy radical.

As examples of these hydrophilic monomers, there may be mentioned acrylic acid, methacrylic acid, maleic acid halfesters with 1-8 carbon atoms in the alcohol radical, N-vinyllactams such as N-vinylpyrrolidone, methacrylamide, N-substituted (meth)acrylamides such as N-methyl- and N-methoxymethyl-(meth)-acrylamide and N-acryloyldimethyltaurine.

Depending on the desired hydrophilic character and swellability of the copolymers and on the length of the polyalkylene oxide chain or chains of the polyfunctional (meth) acrylic ester B, the hydrophilic monomers C are added to the monomer mixture in amounts of 5-60% by weight.

Apart from affecting the hydrophilic character, the addition of these monomers surprisingly also affects the structure of the polymers, which is of very particular advantage in the production of bead polymers, since here the choice of the diluents for the monomer mixture is greatly restricted by the conditions that they should be insoluble in paraffin hydrocarbons and inert towards anhydride groups.

Because of the range of variation in the composition of the monomer mixture, the hydrophilic character, density of crosslinking, swellability and anhydride group content of the copolymers according to the invention can be adapted to give optimal results in the intended particular end use of the preparation over a very broad range.

If desired, there may also be added in addition to the di- and/or poly-(meth)acrylates to be used according to the invention, at least one crosslinking agent having at least two (2) non-conjugated double bonds (e.g. divinyl adipate, methylene-bis-acrylamide, triacrylformal, triallyl cyanurate etc) to the monomer mixture in amounts of 0.01–30% by weight.

The polymerization can be carried out, for example, in an organic solvent, as a precipitation polymerization, in which case the polymers start to precipitate shortly after the start of the polymerization. Inherently, all solvents which are inert towards anhydride groups are suitable. Particularly advantageous solvents are aliphatic, cycloaliphatic and aromatic hydrocarbons and halogen-substituted aromatic and aliphatic hydrocarbons, alkyl-aromatic compounds and carboxylic acid esters.

As examples of suitable organic solvents there may be mentioned: heptane, octane, isooctane, benzine fractions with boiling points of 60° to 200°C., cyclohexane, benzene, toluene, the xylenes, chlorobenzene, dichlorobenzenes, ethyl acetate, butyl acetate, and the like.

The solvent used should preferably possess a boiling point of at least 60°C. and should be easily removable from the precipitation polymer in vacuo. For 1 part of the monomer mixture, about 2–50, preferably 5–20, parts by weight of the solvent are used. The properties of the copolymers, especially the bulk density and the specific surface area, are significantly influenced by the nature and amount of the solvent.

In many cases it is advantageous to use mixtures of the above mentioned solvents or to start the polymerization in a solvent for the polymer and continuously to add a precipitant for the polymer over the course of the polymerization. The precipitant can also be added in one or more portions at particular points in time. Furthermore, the monomer mixture can be fed, together with a suitable initiator, as a solution or without solvent, into a previously taken amount of solvent, so that during the polymerization a uniform low monomer concentration is maintained. Products with swellability, density and specific surface area suited to the particular end use, and with good mechanical stability, having a very wide range of properties, can be produced by using (meth)acrylic monomers B of differing hydrophilic character and varying the polymerization conditions.

The copolymers used according to the invention are preferably produced by suspension polymerization. The most customary type of bead polymerization, in which the monomers, optionally with the addition of an organic solvent, are suspended in water, can in this case only be used with little success, since the anhydride hydrolyzes very rapidly and the resulting dicarboxylic acid mainly passes into the water phase, only small amounts being incorporated into the polymer. Hence, the suspension polymerization is preferably carried out in an organic medium. Paraffin hydrocarbons, such as hexane, heptane, octane and higher homologues, cycloaliphatic compounds such as cyclohexane, and paraffin mixtures such as benzine fractions or paraffin oil, are particularly suitable as the continuous phase. The monomers and the initiator are generally dissolved in a solvent which is immiscible with paraffins and inert towards anhydride groups, such as, for example, acetonitrile, dimethylformamide, dimethylsulphoxide or hexamethylphosphoric acid triamide, and dispersed in the continuous phase, in most cases with addition of at least one dispersing agent. The volume ratio of continuous phase: monomer phase is generally 1:1 to 10:1, preferably 2:1 to 5:1.

In order to stabilize the suspension, it is possible to use, for example, glycerine monooleate and dioleate, as well as mixtures of these compounds, sorbitan monooleate and trioleate or monostearate and tristearate, polyethylene glycol monoethers with stearyl alcohol or lauryl alcohol or nonylphenol, polyethylene glycol monoesters with oleic acid, stearic acid and other fatty acids with more than 10 carbon atoms, and the sodium salt of sulphosuccinic acid dioctyl ester. These stabilizing substances are generally employed in amounts of, preferably 0.1–10% by weight relative to the monomer mixture and are generally dissolved in the hydrocarbon phase. The particle size of the copolymeric product can be reduced either by increasing the speed of stirring or by adding 0.01–2% by weight relative to monomer, of a further surface-active substance, for example an alkylsulphonate.

Polymerization in the process of the invention is initiated by radical initiators. Suitable initiators are, for example, azo compounds or per-compounds. The most customary azo compound for initiating the polymerization is azoisobutyronitrile. Possible per-compounds are mainly diacyl peroxides such as dibenzoyl peroxide or percarbonates such as diisopropyl percarbonate and dicyclohexyl percarbonate, but it is also possible to use dialkyl peroxides, hydroperoxides and redox systems which are active in organic solvents for the initiation.

The initiators are generally added in amounts of 0.01–10 wt. %, preferably 0.1–3 wt. %, relative to the weight of the monomer mixture.

The polymerization is generally carried out at temperatures of about 20°–200°C., preferably 50°14 100°c., depending on the speed of decomposition of the initiators and, in most cases, below the boiling point of the solvent, and in the case of bead polymerizations, below the miscibility temperature of the two phases. Furthermore, it is as a rule advantageous to carry out the polymerization in an inert atmosphere in the absence of oxygen.

The copolymers obtained by precipitation polymerization are colorless to pale yellow-colored powdery substances with bulk volumes of 1.5–30 ml/g, preferably 2–20 ml/g and specific surface areas of 0.1–500 $m^2/g$, preferably 1–400 $m^2/g$. The content of carboxyl groups determined titrimetrically after saponification of the anhydride groups is about 0.01–14 m-equiv/g, preferably about 0.02–11 m-equiv/g.

The copolymers obtained by suspension polymerization are white or slightly colored beads which can in some cases be irregular in shape and have a diameter of 0.03–3 mm, preferably 0.05–0.5 mm and bulk volumes of 1.4–8 ml/g, preferably 1.4–5 ml/g. Their carboxyl group content, determined after hydrolysis of the anhydride groups, is 0.01–14 m-equiv/g, preferably 0.02–11 m-equiv/g.

The copolymers used according to the invention contain copolymerized units essentially in statistical distribution (random copolymers). Because of their high density of crosslinking, they are insoluble in all solvents. Molecular weights can therefore not be determined.

The copolymers can swell in water to between 1.1 and 3 times their bulk volume. They are outstandingly suitable for use as carrier resins for fixing substances which can react with the anhydride groups of the copolymers. They also possess excellent mechanical stability and hence practically no abrasion.

The carrier copolymers described above bind all substances which carry a functional group which is capable of reacting with the anhydride groups of the polymer. In the case of proteins and peptides, these are primarily the terminal amino groups of lysine and the free amino groups of the peptide chain ends.

The following substances are examples of peptide materials which can be bound to the copolymers according to the invention:

Enzymes: Hydrolyases such as proteases, for example trypsin, chymotrypsin, papaine and elastase; amidases, for example asparaginase, glutaminase and urease; acyltransferases, for example penicillinacylase; lyases, for example hyaluronidase.

Other proteins: plasma constituents and globulins (antibodies).

Oligopeptides, such as glutathione.

Polypeptides, such as kallikrein inhibitor and insulin.

Aminoacids, such as lysine or alanine.

It is however envisaged that the invention will primarily be used for proteins isolated from bacteria, fungi, actinomycetes or animal material.

After production of the copolymer, it is combined with the peptide material in a second step. In this step, the requisite amount of polymer is introduced into a stirred aqueous solution of the peptide material at a temperature of between 0° and 30°C. The weight ratio of peptide materials to carrier resin can be varied within wide limits and be suited to the subsequent end use. Good yields are obtained for example with a ratio of 1 part by weight of protein to between 4 and 10 parts by weight of polymeric carrier. However, the optimum ratios depend both on the composition and sturcture of the polymer and on the nature of the protein.

In the case of numerous enzymes it is also advisable to add stabilizers. As such stabilizers, it is possible to use polyethylene glycols or non-ionic wetting agents for reducing denaturation at surfaces, as well as the known SH-reagents or metal ions in the case of special enzymes. The pH is appropriately kept by means of a pH-stat at the optimum pH-value for the particular bonding. This pH-value lies in a range of 2 to 9, preferably 5 to 7. When the peptide material is penicillinacylase it has proved advisable to work at between pH 5.7 and pH 6.8. In doing so, inorganic bases (for example caustic alkali solutions), or organic bases (for example tertiary organic amines), must be added in order to keep the pH-value constant. The progress of the reaction is discernible from the consumption of the amount of base required to keep the pH constant. At room temperature, about 16 hours are required to complete the reaction and at 4°C. up to 40 hours are required. Thereafter, the copolymer is filtered off and is washed with buffers or salts, in the concentration range of 0.2 to 1 M, in order to dissolve off a small proportion of ionically bound protein.

The bound substance can be determined either by elementary analysis or, in the case of enzymes or inhibitors, by the enzymatic activity or the inhibition of the enzymatic activity. The yields of bound substance depend on the nature of the substance and the composition of the polymer. Thus, for example, aminoacids and low molecular peptides were coupled practically completely; however, even with the proteins, the yields of bound enzymatic activity are between about 20 and over 90% of the activity introduced at start.

According to the state of the art (German Offenlegungsschriften 1 935 711 and 2 008 990), the coupling of proteins is effected in buffer solutions in concentrations of 0.05 M to 0.2M. If no buffer is used, the proportion of ionically bound protein increases (German Offenlegungsschrift 1 935 711). Surprisingly it was found that with the preparations according to the invention the coupling in a medium which is as free of ions as possible gives maximum yields of enzyme bound by covalent bonds. In practice a conduction range of 0.1 – 1 m mhos at pH 6.3 was achieved. In this procedure the pH can be kept constant very accurately at the optimum value by means of a pH-stat.

The use of copolymer-bound enzymes is industrially of particular importance since industrially valuable products can be manufactured with their aid. The prior bonding of biological catalysts in accordance with the present process permits them to be isolated completely from the reaction mixture by very simple separation processes and makes it possible to reuse them repeatedly, which is a decisive factor economically. Additionally, in most cases the stability of the sensitive and expensive proteins is decisively improved.

The following gives some examples of the use of the preparations of the invention in carrying out enzyme-catalyzed conversions in accordance with the present invention.

The proteases, such as trypsin, chymotrypsin, papaine and elastase, can be used, for example, for the production of protein hydrolysis products for microbiological processes. Furthermore, the enzymes can also be used to remove antigenic proteins from pharmaceutically active substances.

Acylases are used industrially for the manufacture of 6-aminopenicillanic acid from penicillins or for the separation of racemates of acylated aminoacids. Carrier-bound amylase according to the invention can be used for the hydrolytic degradation of starch.

Special hydrolases, such as asparaginase or urease, can be employed therapeutically, in the copolymer-bound form, on extra-corporal circulation.

These and numerous other possible uses have been described in the literature. See, for example, the summaries in Chem. Eng. News of 15.2.1971, page 86 and Rev. Pure & Appl. Chem. 21, 83 (1971).

A further large field of use for substances fixed to carriers is affinity chromatography. Thus antibodies can be isolated by means of bound antigens or haptens, and conversely antigens can be isolated with fixed antibodies ($\gamma$-globulins). Equally, enzymes can be enriched specifically with the aid of bound inhibitors or substrate analogues. For example, it is shown to isolate trypsin and chymotrypsin by means of bound vegetable or animal inhibitors. Other examples are the isolation of peptidases on special bound peptides or the isolation of plasmin with lysine bound to a carrier. Summarizing works of this field of use have been published by G. Feinstein in Naturwissenschaften 58, 389 (1971) and F. Fried in Chromatographic Reviews 14, 121, (1971).

In order to produce 6-aminopenicillanic acid (6-APA), penicillins can be split by means of acylases from microorganisms, for example, bacteria, especially *E. coli*, Erwinia, Actinomycetes such as *Streptomyces*, *Micromonospora* and *Nocardia;* fungi such as Fusarium; and yeasts.

According to the process of German Patent Specification 1,111,778 for the production of 6-APA, a penicillin G solution is treated with a bacterial sludge which contains the enzyme penicillinacylase (E.C. 3.6.1.11). As a result of the action of the enzyme, the lateral carbonamide grouping of the penicillin is split off without opening the $\beta$-lactam ring.

The use of suspensions of micro-organisms has the following disadvantages:

a. The suspension of micro-organisms, in addition to containing the intra-cellular penicillinacylase, contains further proteins and enzymes as well as constituents from the nutrient medium or their transformation products which have been produced during the fermentation. The impurities cannot be completely eluted from the crystalline 6-APA during working up.

b. The suspension of micro-organisms can economically appropriately only be employed once.

c. The suspension of micro-organisms contains impurities and other enzymes which inactivate penicillin and/or 6-APA by opening the $\beta$-lactam ring.

d. The suspension only contains small amounts of penicillinacylase. The use of more enzyme material, for example to achieve shorter reaction times and hence better 6-APA yields with a lower content of extraneous products is not possible to practice.

e. The operating yields of 6-APA depend on the varying formation of penicillinacylase in the individual fermentation batches.

f. The complete removal of suspended micro-organisms requires an additional process step when working up the 6-APA batches and this causes losses in yield. Further purification steps are necessary to remove protein-like impurities which can cause allergic reactions (British Pat. Nos. 1,169,696, 1,078,847 and 1,114,311).

All disadvantages mentioned are avoided if instead of a suspension of micro-organisms a penicillinacylase is used which is obtained by covalent bonding to a water-insoluble carrier.

While attempts to produce 6-APA by enzymatic splitting of penicillins with carrier-bound penicillinacylase are known, (see on the subject, German Offenlegungsschrift 1 917 057 and German Offenlegungsschrift 1 907 365) it has not been possible to apply the process described on a technical scale. The reasons for this are firstly the mechanical properties of the carrier material used, which is very vulnerable to abrasion, while with moderate process yields only low specific activities of carrier-bound penicillinacylase were achievable.

The insoluble enzyme used in German Pat. application No. 2 157 970, which was obtained by covalent bonding of the penicillinacylase to a copolymer of acrylamide, N,N'-methylene-bis-acrylamide and maleic anhydride, also has disadvantages for the splitting of penicillin on an industrial scale, since it swells strongly and is mechanically unstable. These disadvantages handicap the repeated reuse of the resin, thus manufactured, on an industrial scale. It has now been found that the disadvantages mentioned are avoided if a preparation according to the invention comprising a penicillinacylase bound to a water-insoluble carrier is used for splitting penicillins.

The splitting of penicillins with carrier-bound penicillinacylase according to the invention can be carried out simply and also on a large industrial scale. In a preferred form of this process, the carrier-bound insoluble enzyme is suspended in a solution containing 75,000–150,000 IU/ml of penicillin [1 mg. of potassium benzylpenicillin G corresponds to 1598 IU (International Units)], for example penicillin G or penicillin V. The enzymatic splitting is carried out at a constant pH value in the range of 6-9, particularly in the range of the pH optimum of the particular bound penicillinacylase, for example at pH 7.8. To neutralize the acyl radical split off, for example of phenylacetic acid or of phenoxyacetic acid, aqueous alkali solutions, for example potassium hydroxide solution or sodium hydroxide solution, or organic amines, preferably triethylamine, are used. The reaction velocity and the completion of the splitting can be seen from the consumption of the base. The penicillinacylase catalyses both the splitting of penicillin to give 6-APA and the resynthesis of the penicillins from the splitting products. The equilibrium depends on the pH value of the medium. At lower pH value the equilibrium is displaced in favor of the starting product, penicillin. This can be utilized for the transacylation of penicillins in the presence of other acyl radicals or for the synthesis of penicillins from 6-APA.

The reaction temperature of the enzymatic splitting is preferably 38°C. At lower temperatures, the activity of the enzyme decreases. If the splitting is carried out, for example, at 25°C., twice as much enzyme as at 38°C. has to be employed if the same reaction times are to be achieved.

At a given temperature, the reaction velocity depends on the specific activity and on the amount of the carrier-bound penicillinacylase. Furthermore, the reaction velocity depends on the ratio of the amount of the carrier-bound penicillinacylase to the concentration of the penicillin. A splitting batch with a concentration of 100,000 IU/ml of potassium penicillin G has been completely hydrolyzed to 6-APA and phenylacetic acid after 10 hours at pH 7.8 and 38°C. if, per unit of penicillinacylase, $3.10^5$ units of penicillin G are employed [one enzyme unit (U) is defined as the activity which hydrolyzes 1 $\mu$mol of 6-nitro-3-(phenyl-acetyl)-aminobenzoic acid (NIPAB) per minute at 25°C.]. The proportion of dry enzyme resin is only 0.5–1% of the reaction mixture. If 2 units of penicillinacylase are employed per $10^5$ IU of penicillin G, the complete splitting only requires 2 hours. Even shorter reaction times are also possible when using even more bound penicillinacylase, when using, for example, carrier-bound penicillinacylase from crystallized enzyme.

The carrier-bound penicillinacylase produced according to the invention is preferably in the shape of beads and is distinguished by high mechanical stability and a comparatively high specific gravity. These properties allow it to be employed for prolonged periods of time if it is repeatedly used. These properties furthermore make it possible, in batch processes, to emply intensive stirring and simple separation by centrifuging without loss through mechanical stress, for example through abrasion. Thus, batch processes yield clear filtrates which can, without additional filtration, be processed further in order to isolate the end product, 6-APA. The carrier-bound penicillinacylase produced according to the invention also permits rapid and simple filtration, since, as a result of the mechanical stability, no very fine particles which block the filter surface are produced. The resin offers further advantages in the batch process because of the comparatively high specific gravity, which causes the resin to settle out rapidly, so that after completion of the process the supernatant solution can easily be siphoned off. This results in a simplification of the conduct of the process, since in the batch process the resin can remain in the reaction vessel and be used directly for the next splitting.

The properties of the polymer furthermore permit the use of the carrier-bound penicillinacylase not only in batch processes but also in continuous processes, for example in reaction columns, where the bead shape permits the requisite high speed of flow through the column.

After separating off the enzyme resin, the 6-APA formed in the enzymatic splitting can be isolated from the reaction solution in accordance with known processes (see, for example, German Pat. Specification 1,111,778) and is crystallized at pH 4.3. In the splitting of penicillin, according to the invention, with the carrier-bound penicillinacylase produced according to the invention, substantially higher yields of 6-APA are obtained than when using E. coli sludge, but also higher yields than when using the enzyme resin according to German Patent Application P 2 157 970.4. Thus, as is shown in Examples 14 to 17, 6-APA has been isolated in a yield of about 90% of theory. The 6-APA thus produced does not contain any proteins as impurities. The 6-APA thus produced also contains practically no polymers which can be produced in other procedures. Allergic side-effects attribute to proteins or polymers are impossible with the 6-APA produced according to the invention.

The carrier-bound penicillinacylase produced according to the invention can be used repeatedly over a prolonged period of time. Even thereafter, the enzyme activity is still retained practically completely.

Our copending Application Ser. No. 345,792 filed Mar. 28, 1973, discloses and claims new preparations generally similar to those of the present invention, but lacking residues C.

The boiling points in the Examples were determined at normal pressure. The following examples are presented to illustrate the invention but it is not to be considered as limited thereto.

EXAMPLE 1a 70 g of tetraethylene glycol dimethacrylate, 20 g of methacrylic acid, 10 g of maleic anhydride and 1 g of azoisobutyronitrile are dissolved in 1 liter of benzene and initially polymerized for 4 hours at 60°C. 1 g of azoisobutyronitrile and 200 ml of benzine (boiling point 100°–140°C.) are then added and the polymerization is carried out for 2 hours at 70°C. and 2 hours at 80°C.

The pulverulent polymer is thoroughly washed with petroleum ether (boiling point 30°–50°C.) and dried in vacuo.

Yield: 96 g
Bulk volume: 8.8 ml/g
Swelling volume in water: 12.4 ml/g

Specific surface area: 8.6 m²/g
Acid content after saponification of the anhydride groups = 3.85 m-equiv/g.

EXAMPLE 1b 6 g of the carrier copolymer produced according to Example 1a are suspended in a solution of 610 U of penicillinacylase in 150 ml of water. The pH value is kept at 6.3 by adding 1 N NaOH, using a pH-stat, and the suspension is stirred for 20 hours at 25°C.

The copolymer is then filtered off on a G 3 glass frit and washed with 300 ml of 0.05 M phosphate buffer of pH 7.5, containing 1 M sodium chloride, and with 300 ml of the same buffer without sodium chloride. No further activity can be eluted by further washing. The supernatant liquid and the wash solutions are combined and their enzymatic activity is determined. The enzymatic activity of the moist copolymer is measured in aliquot amount.
Result:
Enzymatic activities (NIPAB test):
Starting solution     610 U
Supernatant liquid + wash solutions    112 U
Carrier copolymer after the reaction    561 U
(i.e. 92% of the starting activity)

The enzymatic activity of the penicillinacylase is measured colorimetrically or titrimetrically with 0.002 M of 6-nitro-3-(N-phenylacetyl)-aminobenzoic acid (NIPAB) as the substrate at pH 7.5 and 25°C. The molar extinction coefficient of the resulting 6-nitro-3-aminobenzoic acid is $E_{405\ nm} = 9{,}090$. 1 unit (U) corresponds to the conversion of 1 $\mu$mol of substrate per minute.

EXAMPLE 1c 400 mg of the carrier copolymer produced according to Example 1a are suspended in a solution of 40 ml of urease in 32 ml of water. The pH value is kept constant at pH 6.0 by adding 1 N sodium hydroxide solution, while constantly stirring at room temperature. After 16 hours, the reaction is complete and the copolymer is filtered off and washed with buffer as in Example 1 (b).
Result:
Enzymatic activity:
Starting solution    168 U
Supernatant liquid + wash solutions    64.5 U
Carrier copolymer after the reaction    87 U
(i.e. 52% of the starting activity)

The enzymatic activity of the urease is determined titrimetrically with 0.17 M urea as the substrate, at 25°C. and pH 6.1. 1 unit (U) corresponds to the amount of enzyme which consumes 1 $\mu$mol of urea, that is to say 2 $\mu$mol of hydrochloric acid, per minute.

EXAMPLE 1d 500 mg of the carrier copolymer produced according to Example 1a are suspended in a solution of 100 mg of trypsin in 32 ml of 0.02 M calcium chloride. The pH value is kept constant at pH 6.3 by addition of 1 N sodium hydroxide solution while constantly stirring at 4°C. After 16 hours the copolymer is filtered off and washed with buffer as in Example 1b.
Result:
Enzymatic activity:
Starting solution    110 U
Supernatant liquid + wash solutions    15.6 U
Carrier copolymer after the reaction    64 U
(i.e. 58% of the starting activity)

The enzymatic activity was determined colorimetrically according to Tuppy. Z. Physiol. Chem. 329 (1962) 278, with benzoyl-arginine-p-nitroanilide (BAPNA) as the substrate. 1 unit (U) corresponds to the splitting of 1 $\mu$ mol of substrate per minute at 25°C. and pH 7.8.

EXAMPLE 2a

A solution of 80 g of tetraethylene glycol dimethacrylate, 10 g of methacrylic acid, 10 g of maleic anhydride and 1 g of azoisobutyronitrile in 1 liter of benzene is polymerized for 4 hours at 60°C., 2 hours at 70°C. and 1 hour at 80°C., while stirring slowly. The polymer is filtered off, stirred 3 times in benzene, washed with petroleum ether and dried in vacuo.
Yield: 70 g
Bulk volume: 7.0 ml/g
Swelling volume in water: 8.2 ml/g
Specific surface area: 5.3 m²/g
Acid content after saponification of the anhydride groups = 2.55 m-equiv/g.

EXAMPLE 2b 1 g of the polymer produced according to Example 2a is reacted, analogously to Example 1b, with penicillinacylase in 33 ml of water at pH 6.3.
Result:
Enzymatic activities (NIPAB test):
Starting solution    118 U
Supernatant liquid + wash solutions    21 U
Carrier copolymer after the reaction    82 U
(i.e. 69% of the starting activity)

EXAMPLE 3a 60 g of tetraethylene glycol dimethacrylate, 30 g of methacrylic acid, 10 g of maleic anhydride and 1 g of azoisobutyronitrile are dissolved in 300 ml of acetonitrile. This solution is suspended in 1 liter of benzine (boiling point 100°–140°C.) which contains 5 g of a mixture of glycerine monooleate and glycerine dioleate and is polymerized for 22 hours at 60°C.

The polymer beads are filtered off, suspended three times in benzene and subsequently twice in petroleum ether (boiling point 30°–50°C.) and dried in vacuo.
Yield: 94 g of white spheres
Bulk volume: 4.4 ml/g
Swelling volume in water: 5.5 ml/g
Specific surface area: 6.6 m²/g
Mean particle diameter: ~ 200 $\mu$
Acid content after saponification of the anhydride groups = 4.3 m-equiv/g.

EXAMPLE 3b 1 g of the polymer produced according to Example 3 (a) is reacted analogously to Example 1 (b) with penicillinacylase in 33 ml of water at pH 6.3.
Result:
Enzymatic activity (NIPAB test):
Starting solution    118 U
Supernatant liquid + wash solutions    43 U
Carrier copolymer after the reaction    96 U
(i.e. 81% of the starting activity)

EXAMPLE 4a

A solution of 2,100 g of tetraethylene glycol dimethacrylate, 600 g of methacrylic acid, 300 g of maleic anhydride and 30 g of azoisobutyronitrile in 7.5 liters of acetonitrile is suspended in 21 liters of benzine (boiling point 100°–140°C.) in which 150 g of a mixture of glycerine monooleate and glycerine dioleate have been dissolved, and is polymerized for 1 hour at 50°C. and 20 hours at 60°C.

The bead polymer is filtered off, twice stirred with toluene and once with petroleum ether (boiling point 30°–50°C.) and dried at 60°C.
Yield: 2.95 kg
Bulk volume: 4.7 ml/g
Swelling volume in water: 5.4 ml/g
Mean particle diameter: approx. 0.3 mm
Acid content after saponification of the anhydride groups = 4.0 m-equiv/g.

EXAMPLE 4b 1 g of the polymer produced according to Example 4a is reacted as described in Example 1b with penicillinacylase in 33 ml of water at pH 6.3.
Result:
Enzymatic activity (NIPAB test):
  In the starting solution      107 U
  Supernatant liquid and wash solutions   27 U
  Carrier copolymer after the reaction    67 U (i.e. 63% of the starting activity)

EXAMPLE 4c 20 g of the polymer produced according to Example 4 (a) are introduced into 600 ml of a solution of 1.0 g of nonspecific elastase from pig pancreas at room temperature, while stirring. At the same time the pH is kept constant at 5.8. After a reaction time of 16 hours, the copolymer is filtered off and worked-up in the manner described in Example 1 (b).
Result:
Enzymatic activity (casein test):
  Starting solution       2,180 U
  Supernatant liquid + wash solutions    993 U
  Carrier copolymer after the reaction    1,225 U (i.e. 56% of the starting activity)

The enzymatic activity of the nonspecific elastase is determined titrimetrically with casin as the substrate (concentration 11.9 mg/ml) at pH 8.0 at 25°C. 1 unit (U) corresponds to a consumption of 1 μmol of potassium hydroxide solution per minute.

EXAMPLE 5a

A solution of 80 g of tetraethylene glycol dimethacrylate, 10 g of methacrylic acid, 10 g of maleic anhydride and 1 g of azoisobutyronitrile in 300 ml of acetonitrile is polymerized as described in Example 3a.
Yield: 92 g of white, egg-shaped particles
Bulk volume: 2.5 ml/g
Swelling volume in water: 3.2 ml/g
Specific surface area: 1.7 m²/g
Mean particle diameter: 125 μ
Acid content after saponification of the anhydride groups = 3.5 m-equiv/g.

EXAMPLE 5b 1 g of the polymer produced according to Example 5a is reacted as described in Example 1b with penicillinacylase in 33 ml of water at pH 6.3.
Result:
Enzymatic activity (NIPAB test):
  Starting solution    118 U
  Supernatant liquid + wash solutions   34 U
  Carrier copolymer after the reaction    61 U (i.e. 52% of the starting activity)

EXAMPLE 6a

A solution of 50 g of ethylene glycol dimethacrylate, 40 g of methacrylic acid, 10 g of maleic anhydride and 1 g of azoisobutyronitrile in 300 ml of acetonitrile is suspended in 1 liter of benzine (boiling point 100°–140°C.) in which 5 g of a mixture of glycerine monooleate and glycerine dioleate are dissolved, and is polymerized for 20 hours at 60°C. The bead polymer is filtered off, suspended three times in benzene and twice in petroleum ether (boiling point 30°–50°C.) and dried in vacuo at 50°C.
Yield: 87 g
Bulk volume: 4.8 ml/g
Swelling volume in water: 5.6 ml/g
Specific surface area: 13.2 m²/g
Acid content after saponification of the anhydride groups = 4.2 m-equiv/g.

EXAMPLE 6b 1 g of the polymer produced according to Example 6a is reacted as described in Example 1b with penicillinacylase in 33 ml of water at pH 6.3.
Result:
Enzymatic activity (NIPAB test):
  Starting solution    118 U
  Supernatant liquid and wash solutions    29 U
  Carrier copolymer after the reaction    55 U (i.e. 47% of the starting activity)

EXAMPLE 7a

A solution of 50 g of trimethylolpropane trimethacrylate, 30 g of methacrylic acid, 20 g of maleic anhydride and 1 g of azoisobutyronitrile in 300 ml of acetonitrile is polymerized as described in Example 6a.
Yield: 86 g
Bulk volume: 2.0 ml/g
Swelling volume in water: 2.2 ml/g
Mean particle diameter: ~30 μ
Acid content after saponification of the anhydride groups = 4.1 m-equiv/g.

EXAMPLE 7b 1 g of the copolymer produced according to Example 7a is added to a solution of 100 mg of lysine in 32 ml of water at room temperature, with constant stirring. The pH value is kept constant at 6.3. After 16 hours, the copolymer is filtered off, suspended in 50 ml of 1 M sodium chloride solution, filtered off and rinsed with 100 ml of water. The residue is dried in vacuo at 100°C. and the nitrogen content is determined by Kjeldahl's method.
Result:
  Dry weight: 860 mg
  Nitrogen content: 1.5%, corresponding to a content of 65 mg of the lysine in the copolymer. This represents 65% of the amount of lysine employed.

EXAMPLE 8

The following were polymerized as described in Example 6a (variation of the amount of the maleic anhydride):

| Experiment No. | a | b | c | d | e | f | g |
|---|---|---|---|---|---|---|---|
| TGDM (g) | 75 | 70 | 65 | 60 | 55 | 50 | 45 |
| MAA (g) | 20 | 20 | 20 | 20 | 20 | 20 | 20 |
| MA (g) | 5 | 10 | 15 | 20 | 25 | 30 | 35 |
| AIBN (g) | 1 | 1 | 1 | 1 | 1 | 1 | 1 |
| Acetonitrile (ml) | 250 | 250 | 250 | 250 | 250 | 250 | 250 |
| Benzine (ml) | 1,000 | 1,000 | 1,000 | 1,000 | 1,000 | 1,000 | 1,000 |
| Emulsifier (g) | 5 | 2.5 | 5 | 5 | 5 | 5 | 5 |
| Yield (g) | 95 | 93 | 86 | 88 | 80 | 79 | 70 |
| $V_s$ (ml/g) | 3.4 | 3.4 | 3.6 | 2.6 | 3.0 | 3.2 | 2.5 |
| $V_q$ (ml/g) | 4.4 | 6.0 | 4.5 | 3.5 | 4.0 | 4.3 | 3.4 |
| Acid (meq./g) | 3.1 | 4.2 | 3.6 | 3.8 | 3.9 | 4.7 | 4.3 |

TGDM = Tetraethylene glycol dimethacrylate
MAA = Methacrylic acid
MA = Maleic anhydride
AIBN = Azoisobutyronitrile
Emulsifier = Mixture of glycerine monooleate and glycerine dioleate
$V_s$ = Bulk volume
$V_q$ = Swelling volume in water
Acid = Acid content after saponification of the anhydride groups.

EXAMPLE 9a

A solution of 70 g of tetraethylene glycol dimethacrylate, 20 g of acrylic acid, 10 g of maleic anhydride and 1 g of azoisobutyronitrile in 1 liter of benzene is warmed for 4 hours at 60°C., 2 hours at 70° and 2 hours at 80°C., with exclusion of air and while stirring slowly. The finely divided precipitation polymer is suspended three times in benzene and twice in acetonitrile, filtered off and dried in vacuo.

Yield: 94 g
Bulk volume: 6.8 ml/g
Swelling volume in water: 7.6 ml/g
Acid content after saponification of the anhydride groups = 1.64 m-equiv/g

EXAMPLE 9b 1 g of the polymer produced according to Example 9a is reacted as described in Example 1b, with penicillinacylase in 32 ml of water at pH 6.3.
Result:
Enzymatic activity (NIPAB test):
  Starting solution    107 U
  Supernatant liquid + wash solution    26 g
  Carrier copolymer after the reaction    38 U (i.e. 36% of the starting activity)

EXAMPLE 10a

A solution of 50 g of tetraethylene glycol dimethacrylate, 40 g of N-vinylpyrrolidone, 10 g of maleic anhydride and 1 g of dicyclohexyl percarbonate in 200 ml of acetonitrile is suspended in 1 liter of benzine (boiling point 100°–140°C.) which contains 5 g of a mixture of glycerine monooleate and glycerine dioleate and is initially warmed to 50°C. for 18 hours, while stirring. A further 1 g of the initiator is then added and the mixture is stirred for a further 8 hours at 60°C. The polymer spheres are thoroughly washed with benzene and petroleum ether and dried in vacuo. Yield: 54 g of clear beads Bulk volume: 1.6 ml/g
Swelling volume in water: 2.4 ml/g
Mean particle diameter: ~0.3 mm
Acid content after saponification of the anhydride groups = 3.3 m-equiv/g
Nitrogen content: 3.4% Δ 27% of N-vinylpyrrolidone

EXAMPLE 10b 1 g of the polymer produced according to Example 10a is reacted as described in Example 1b with penicillinacylase in 33 ml of water at pH 6.3.
Result:
Enzymatic activity (NIPAB test):
  Starting solution    107 U
  Supernatant liquid + wash solutions    26 U
  Carrier copolymer after the reaction    82 U (i.e. 77% of the starting activity)

EXAMPLE 11a

A solution of 70 g of tetraethylene glycol dimethacrylate, 20 g of methacrylamide, 10 g of maleic anhydride, 1 g of azoisobutyronitrile and 200 ml of acetonitrile is suspended in benzine and polymerized as described in Example 5 (a).
Yield: 93 g
Bulk volume: 2.0 ml/g
Swelling volume in water: 3.3 ml/g
Acid content after saponification of the anhydride groups: 1.7 m-equiv/g

EXAMPLE 11b 1 g of the polymer produced as described in Example 11a is reacted as described in Example 1b with penicillinacylase in 32 ml of water at pH 6.3.
Result:
Enzymatic activity (NIPAB test):
  Starting solution    107 U
  Supernatant liquid and wash solutions    42 U
  Carrier copolymer after the reaction    33 U (i.e. 31% of the starting activity)

EXAMPLE 12a

A solution of 60 g of tetraethylene glycol dimethacrylate, 30 g of N-methoxymethyl-acrylamide, 10 g of maleic anhydride and 1 g of azoisobutyronitrile in 200 ml of acetonitrile is suspended in 1 liter of benzine in which 5 g of a mixture of glycerine monooleate and glycerine dioleate are dissolved, and is polymerized for 20 hours at 60°C.

The bead polymer is filtered off, suspended three times in ethyl acetate and dried in vacuo at 50°C.
Yield: 97 g
Bulk volume: 1.6 ml/g
Swelling volume in water: 3.1 ml/g
Mean particle diameter: ~0.3 mm

EXAMPLE 12b 1 g of the polymer produced according to Example 12a is reacted as described in Example 1b with penicillinacylase in 32 ml of water at pH 6.3.
Result:
Enzymatic activity (NIPAB test):
Starting solution    107 U
Supernatant liquid + wash solutions    49 U
Carrier copolymer after the reaction    25 U (i.e. 23% of the starting activity)

EXAMPLE 13a

If in batch 12 (a) 30 g of N-methoxymethylmethacrylamide are employed instead of N-methoxymethyl-acrylamide, the following result is obtained:
Yield: 94 g
Bulk volume: 2.4 ml/g
Swelling volume in water: 3.9 ml/g
Mean particle diameter: 0.6 mm

EXAMPLE 13b 1 g of the polymer produced according to Example 13a is reacted as described in Examples 1b with penicillinacylase in 32 ml of water at pH 6.3.
Result:
Enzymatic activity (NIPAB test):
Starting solution    107 U
Supernatant liquid and wash solutions    60 U
Carrier copolymer after the reaction    24 U (i.e. 22% of the starting activity)

EXAMPLE 14

76.1 kg (moist weight) of carrier-bound penicillinacylase produced according to Example 4 (b) having an activity of 737,000 U (NIPAB test) and 125 kg of potassium penicillin G (purity 98%) are successively added to 2,000 liters of water and the mixture is stirred at 38°C. The pH value of the reaction batch is kept constant at 7.8 by continuous addition of triethylamine. After 8 hours, no further triethylamine is taken up. The carrier-bound penicillinacylase is centrifuged off, rinsed with 60 liters of water and 80 liters of 0.2 M phosphate buffer of pH 6.5, and reemployed for further splitting batches. The filtrate, including the wash water, is concentrated to 300 liters in vacuo. The 6-APA is precipitated by addition of half-concentrated hydrochloric acid at the isoelectric point at pH 4.3 in the presence of 200 liters of methyl isobutyl ketone. After one hour the product is filtered off and rinsed with 200 liters of water and then with 200 liters of acetone. It is dried in vacuo at 40°C.; melting point 208°C; yield 66.7 kg, representing 91.9% of theory; purity 98%.

The carrier-bound penicillinacylase was successively employed for a total of 30 batches. Even after 30 splitting reactions, the carrier-bound penicillinacylase has not been consumed. The reaction time does not change. Working up took place as described above. The yields of 6-APA achieved are listed below:

| | |
|---|---|
| 1st splitting reaction | 91.9% of theory |
| 2nd splitting reaction | 91.4% of theory |
| 3rd splitting reaction | 91.6% of theory |
| 4th splitting reaction | 91.0% of theory |
| 5th splitting reaction | 91.2% of theory |
| 6th splitting reaction | 90.3% of theory |
| 7th splitting reaction | 91.5% of theory |
| 8th splitting reaction | 90.9% of theory |
| 9th splitting reaction | 91.9% of theory |
| 10th splitting reaction | 90.7% of theory |
| 11th splitting reaction | 91.2% of theory |
| 12th splitting reaction | 90.1% of theory |
| 13th splitting reaction | 90.9% of theory |
| 14th splitting reaction | 90.7% of theory |
| 15th splitting reaction | 91.0% of theory |
| 16th splitting reaction | 90.2% of theory |
| 17th splitting reaction | 90.3% of theory |
| 18th splitting reaction | 89.9% of theory |
| 19th splitting reaction | 89.8% of theory |
| 20th splitting reaction | 89.1% of theory |
| 21st splitting reaction | 91.7% of theory |
| 22nd splitting reaction | 91.9% of theory |
| 23rd splitting reaction | 91.6% of theory |
| 24th splitting reaction | 91.1% of theory |
| 25th splitting reaction | 91.8% of theory |
| 26th splitting reaction | 90.7% of theory |
| 27th splitting reaction | 91.7% of theory |
| 28th splitting reaction | 91.4% of theory |
| 29th splitting reaction | 90.8% of theory |
| 30th splitting reaction | 90.3% of theory |

$\phi = 90.95\%$ of theory

EXAMPLE 15

330 g of carrier-bound penicillinacylase produced according to Example 1, having an enzymatic activity of 3,410 U (NIPAB test) and 129 g of potassium penicillin G are successively added to 2,000 ml of water and stirred at 38°C. and pH 7.8 as described in Example 14. The penicillin G is completely split to 6-APA and phenylacetic acid over the course of 2 hours. The 6-APA is isolated as described in Example 14. The carrierbound penicillinacylase is employed 20 times in succession. Even after the twentieth splitting, the reaction time does not have to be extended to achieve complete splitting.

Yields of 6-APA

| | |
|---|---|
| 1st splitting reaction | 67.5 g (90.1% of theory) |
| 2nd splitting reaction | 68.4 g (91.1% of theory) |
| 3rd splitting reaction | 68.7 g (91.9% of theory) |
| 4th splitting reaction | 68.6 g (91.5% of theory) |
| 5th splitting reaction | 68.4 g (91.0% of theory) |
| 6th splitting reaction | 68.1 g (90.8% of theory) |
| 7th splitting reaction | 68.7 g (91.6% of theory) |
| 8th splitting reaction | 68.4 g (91.2% of theory) |
| 9th splitting reaction | 68.5 g (91.5% of theory) |
| 10th splitting reaction | 68.1 g (90.9% of theory) |
| 11th splitting reaction | 68.5 g (91.3% of theory) |
| 12th splitting reaction | 68.6 g (91.7% of theory) |
| 13th splitting reaction | 68.5 g (91.3% of theory) |
| 14th splitting reaction | 68.1 g (90.8% of theory) |
| 15th splitting reaction | 68.3 g (91.1% of theory) |

16th splitting reaction 67.8 g (90.5% of theory)
17th splitting reaction 68.0 g (90.6% of theory)
18th splitting reaction 67.4 g (89.9% of theory)
19th splitting reaction 67.5 g (90.0% of theory)
20th splitting reaction 66.8 g (89.1% of theory)
$\phi$ = 90.89% of theory

EXAMPLE 16

120 g of carrier-bound penicillinacylase (moist weight) according to Example 4, with an activity of 1,160 U (NIPAB test) and 120 g of potassium penicillin G, are introduced into 1,300 ml of water and stirred for 9 hours at 38°C. and pH 7.8, as described in Example 14. The mixture is worked up as described in Example 14. The carrier-bound penicillinacylase is employed 5 times in succession for the enzymatic splitting reaction. The yields of 6-APS achieved are listed below:

1st splitting reaction 61.2 g (87.6% of theory)
2nd splitting reaction 62.0 g (88.9% of theory)
3rd splitting reaction 63.3 g (90.6% of theory)
4th splitting reaction 62.7 g (89.9% of theory)
5th splitting reaction 63.1 g (90.4% of theory)

EXAMPLE 17

290 g of carrier-bound penicillinacylase according to Example 4, having an enzymatic activity of 2,803 U (NIPAB test) and 138 g of potassium penicillin V are added to 2,000 ml of water and stirred for 9 hours at 38°C. The pH value is kept constant at 7.8 by continuous addition of triethylamine. The mixture is worked up as described in Example 1. Yields of 6-APA 64.3 g (86.1% of theory); purity 97.4%.

the invention has been described herein with reference to certain preferred embodiments. However, as variations thereon will become obvious to those skilled in the art, the invention is not to be considered as limited thereto.

What we claim is:

1. A crosslinked copolymer comprising the following copolymerized units:
   A. about 0.1 to 30 weight percent of at least one $\alpha,\beta$-monoolefinically unsaturated dicarboxylic acid anhydride having 4 to 9 carbon atoms;
   B. about 35 to 90 weight percent of at least one di- and/or poly(meth)acrylate of a diol and/or a polyol; and
   C. about 5 to 60 weight percent of at least one hydrophilic monomer containing a carboxyl, aminocarbonyl, sulfo or sulfamoyl group.

2. A preparation in accordance with claim 1 in which the copolymer also comprises copolymerized units derived from 0.01 to 30 weight percent, based on the total monomer units of the copolymer, of a crosslinking agent having at least 2 non-conjugated double bonds said agent being additional to and other than monomer (B).

* * * * *

UNITED STATES PATENT OFFICE
CERTIFICATE OF CORRECTION

Patent No. 3,941,756   Dated March 2, 1976

Inventor(s) Fritz Huper et al

It is certified that error appears in the above-identified patent and that said Letters Patent are hereby corrected as shown below:

Column 3, line 16-"20°c" should be--20°C--.

Column 5, line 48-"50°14100°C" should be--50°C-100°C--.

Column 6, line 48-"sturcture" should be--structure--.

Column 7, line 53-"on" should be--in--.

Column 19, line 17-"APS" should be--APA--.

Signed and Sealed this

Twenty-seventh Day of July 1976

[SEAL]

Attest:

RUTH C. MASON  
Attesting Officer

C. MARSHALL DANN  
Commissioner of Patents and Trademarks